US010351515B2

(12) United States Patent
Mendes et al.

(10) Patent No.: US 10,351,515 B2
(45) Date of Patent: Jul. 16, 2019

(54) POLYMORPHIC FORMS OF MINOCYCLINE BASE AND PROCESSES FOR THEIR PREPARATION

(71) Applicant: Hovione Scientia Limited, Loughbeg, Ringaskiddy, Cork (IE)

(72) Inventors: Zita Mendes, Lisbon (PT); Constanca Cacela, Lisbon (PT); Gloria Ten Figas, Amsterdam (NL); Ana Fernandez Casares, Amsterdam (NL)

(73) Assignee: Hovione Scientia Limited, Loughbeg, Ringaskiddy, Cork (IE)

( * ) Notice: Subject to any disclaimer, the term of this patent is extended or adjusted under 35 U.S.C. 154(b) by 0 days.

(21) Appl. No.: 15/550,179

(22) PCT Filed: Feb. 12, 2016

(86) PCT No.: PCT/GB2016/050340
§ 371 (c)(1),
(2) Date: Aug. 10, 2017

(87) PCT Pub. No.: WO2016/128760
PCT Pub. Date: Aug. 18, 2016

(65) Prior Publication Data
US 2018/0029977 A1 Feb. 1, 2018

(30) Foreign Application Priority Data

Feb. 13, 2015 (PT) .......................... 108223

(51) Int. Cl.
*C07C 237/26* (2006.01)
*A61K 31/65* (2006.01)
(52) U.S. Cl.
CPC ............ *C07C 237/26* (2013.01); *A61K 31/65* (2013.01); *C07B 2200/13* (2013.01)
(58) Field of Classification Search
CPC .... A61K 31/65; C07C 237/26; C07B 2200/13
See application file for complete search history.

(56) References Cited

U.S. PATENT DOCUMENTS 5,202,449 A * 4/1993 Hasegawa ............. C07C 231/24
552/203

FOREIGN PATENT DOCUMENTS

| WO | 2008102161 A2 | 8/2008 |
| WO | 2009143509 A1 | 11/2009 |
| WO | 2013095169 A1 | 6/2013 |

OTHER PUBLICATIONS

Merck, The Merck Index, 10th Edition, 1983, p. 888. (Year: 1983).*
Singapore Office Action, Application No. SG11201706496P, dated Mar. 29, 2018.
PCT International Search Report and the Written Opinion, Application No. PCT/GB2016/050340 filed Feb. 12, 2016, dated Jul. 14, 2016.
PCT International Preliminary Report on Patent Ability, Application No. PCT/GB2016/050340 filed Feb. 12, 2016, dated May 17, 2017.
EP Search Results, Application No. 108223, dated Feb. 13, 2015.
Haleblian, "Pharmaceutical Applications of Polymorphism", Journal of Pharmaceutical Sciences, Aug. 1969, vol. 58, No. 8, pp. 911-929.

* cited by examiner

*Primary Examiner* — Paul A Zucker
(74) *Attorney, Agent, or Firm* — MacMillan, Sobanski & Todd, LLC

(57) ABSTRACT

The present invention concerns new forms of crystalline minocycline base. In particular, two new crystalline polymorphic forms, designated Form IV and Form V of minocycline base are provided. These are characterized by XRD, FTIR and TGA. Processes for preparing the new polymorphic forms and their use in pharmaceutical compositions are also provided. Form IV and form V are prepared by dissolving and/or suspending minocycline base in an organic solvent followed by crystallization.

14 Claims, 9 Drawing Sheets

POLYMORPHIC FORMS OF MINOCYCLINE BASE AND PROCESSES FOR THEIR PREPARATION

The present invention claims the benefit of the PCT/GB2016/050340 filed 12 Feb. 2016, which claims priority to PT/108223 filed 13 Feb. 2015.

INTRODUCTION

The present invention provides two new polymorphic forms of crystalline minocycline base, with improved solubility profiles and a favorable log P and also describes processes to obtain crystalline minocycline base polymorphic forms. These characteristics make these new polymorphic forms more suitable for use in pharmaceutical formulations.

BACKGROUND OF THE INVENTION

Minocycline is a member of the broad spectrum tetracycline antibiotics, which has a broader spectrum than the other members of this group of compounds.

Minocycline is widely used in therapy, primarily to treat acne and rosacea at a once daily dose of 100 mg. Minocycline has a unique biological activity profile: it has both antibacterial and anti-inflammatory proprieties.

The preparation of minocycline is, for example, disclosed in U.S. Pat. Nos. 3,148,212; 3,226,436 and 4,849,136.

In general minocycline may be used as the base per se or, for example, as acid addition salt thereof. Until 2008 minocycline base, was known only in the amorphous form.

WO2008102161 describes three crystalline forms of minocycline base which are more stable than the previously known amorphous product.

SUMMARY OF THE INVENTION

We have now discovered further new crystalline forms with a better solubility profile and a favorable log P, and these forms have been found to further improve bioavailability and ease of formulation.

According to the present invention, there is provided crystalline minocycline base form IV as described herein. It is, in particular, characterized by an X-ray powder diffraction pattern having peaks at 8.3; 13.46; 14.1, 21.3; 16.62±0.2° 2θ. It can be further characterized by an X-ray powder diffraction pattern having peaks at 7.06, 8.3, 10.3, 11.18, 13.46, 14.1, 14.94, 16.62, 20.62, 21.3, ±0.2° 2θ.

Crystalline minocycline base form IV is suitably characterized by an X-ray powder diffraction pattern having peaks as given in FIG. 1.

Crystalline minocycline base form IV according to the invention preferably shows an endotherm at 146° C. from the STDA signal of a TGA analysis as described herein.

The invention also provides minocycline acid addition salts formed from, or obtainable from, crystalline minocycline base form IV according to the invention.

In another aspect, there is provided a process for preparing minocycline base form IV according to the invention and this is preferably characterized by comprising dissolving minocycline base in an aliphatic ketone having 8 carbon atoms or less, or 6 carbon atoms or less, followed by the precipitation of, and optionally isolation of, form IV. We prefer to use aliphatic secondary ketones. Aliphatic ketones having 4 carbon atoms are preferred. One preferred aliphatic ketone is methyl ethyl ketone (MEK).

The process for preparing minocycline base form IV according to the invention is preferably characterized by a dissolution/precipitation temperature of from 20 to 25° C. The solution is stirred for at least 30 mins, before any isolation. The solution may, for example, be stirred up to 5 hours, or up to 10 hours, in order to increase the yield of precipitate.

In another aspect of the invention, there is provided crystalline minocycline base form V characterized, in particular, by an X-ray powder diffraction pattern having peaks at 5.34, 16.74, 21.06, 23.02, 22.26±0.2° 2θ. It is further characterized by an X-ray powder diffraction pattern having peaks at 2.9, 5.34, 7.9, 12.94, 15.06, 16.74, 18.22, 19.78, 21.06, 22.26, 23.02, 25.42±0.2° 2θ.

Crystalline minocycline base form V according to the invention is suitably characterized by an X-ray powder diffraction pattern having peaks as given in FIG. 4.

Crystalline minocycline base form V according to the invention preferably shows an endotherm at 140° C. from the STDA signal of a TGA analysis as described herein.

The invention also provides minocycline acid addition salts formed from, or obtainable from, crystalline minocycline base form V according to the invention.

The invention also provides a process for preparing minocycline base form V according to the invention characterized by suspending minocycline base in 2-methyl tetrahydrofuran (THF) and applying a thermocycling temperature profile for crystallization, optionally followed by isolation of the crystals.

Preferably, the thermocycling temperature profile comprises heating the suspension three times up to a temperature of about 40° C. (+/−5° C.) and cooling each time to about 5° C. (+/−5° C.). The thermocycling profile shown in FIG. 8 illustrates a suitable regime.

The invention also provides a pharmaceutical composition characterized by comprising crystalline minocycline base form IV, or an acid addition salt thereof, according to the invention, and optionally one or more pharmaceutically acceptable excipients.

The invention also provides a pharmaceutical composition characterized by comprising crystalline minocycline base form V, or an acid addition salt thereof, according to the invention, and optionally one or more pharmaceutically acceptable excipients. Acceptable excipients, as well as the types of formulation suitable for delivery of minocycline, will be known to those familiar with this technical area.

The invention also provides a pharmaceutical composition as described herein for use in medicine. Preferably, the pharmaceutical composition is used as an antibacterial agent or as an anti-inflammatory agent.

DETAILED DESCRIPTION

The present invention describes two new crystalline minocycline base forms. The present inventors have now found that, surprisingly, minocycline base can be provided in new stable crystalline forms with improved bioavailability and ease of formulation.

In one aspect, polymorphic Form IV of crystalline minocycline base is provided. This is a new crystalline form of minocycline base with improved bioavailability and ease of formulation.

Figure 1:
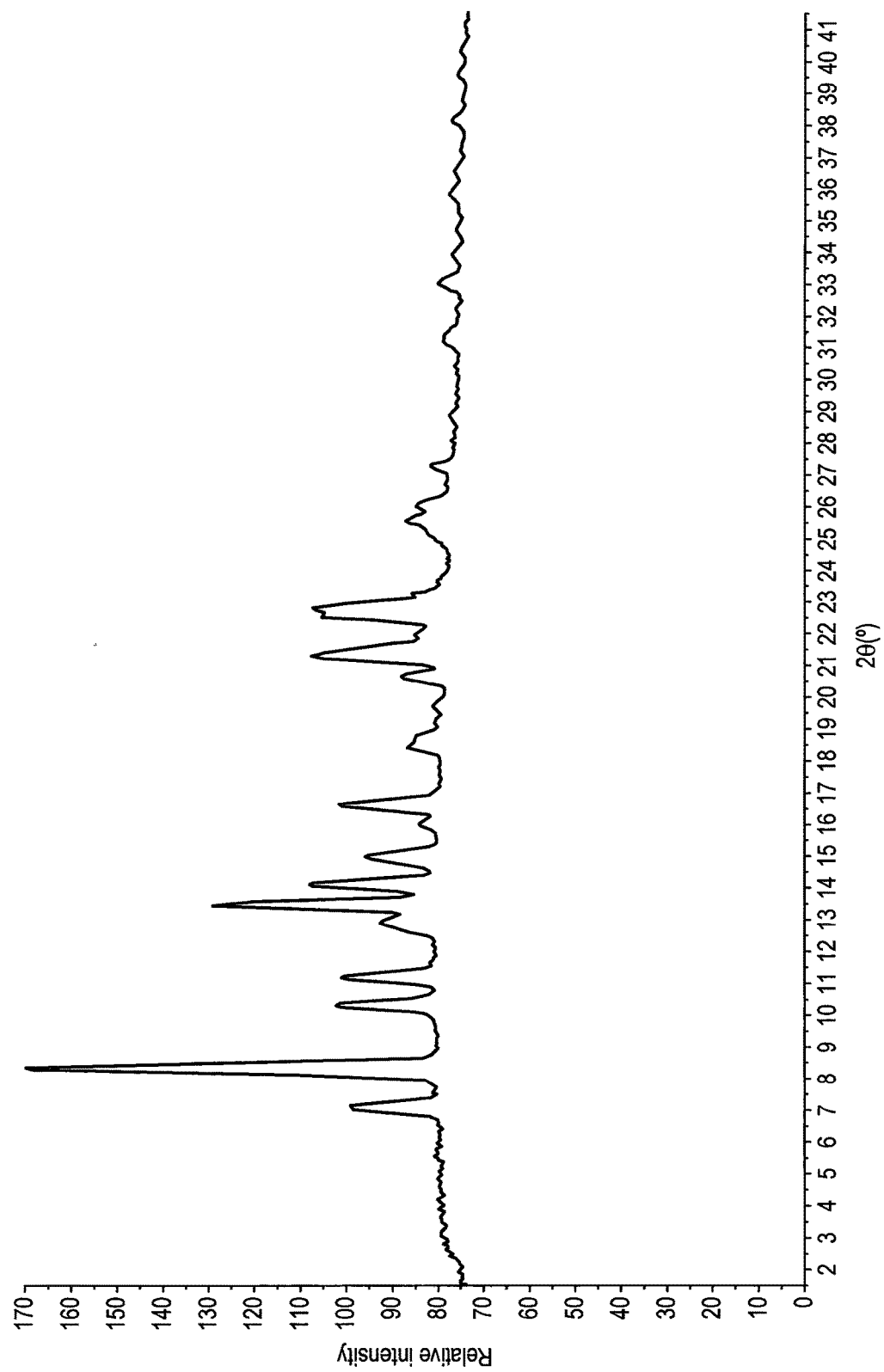
FIG. 1: Crystalline minocycline base form IV is suitably characterized by an X-ray powder diffraction pattern having peaks.
Figure 2:
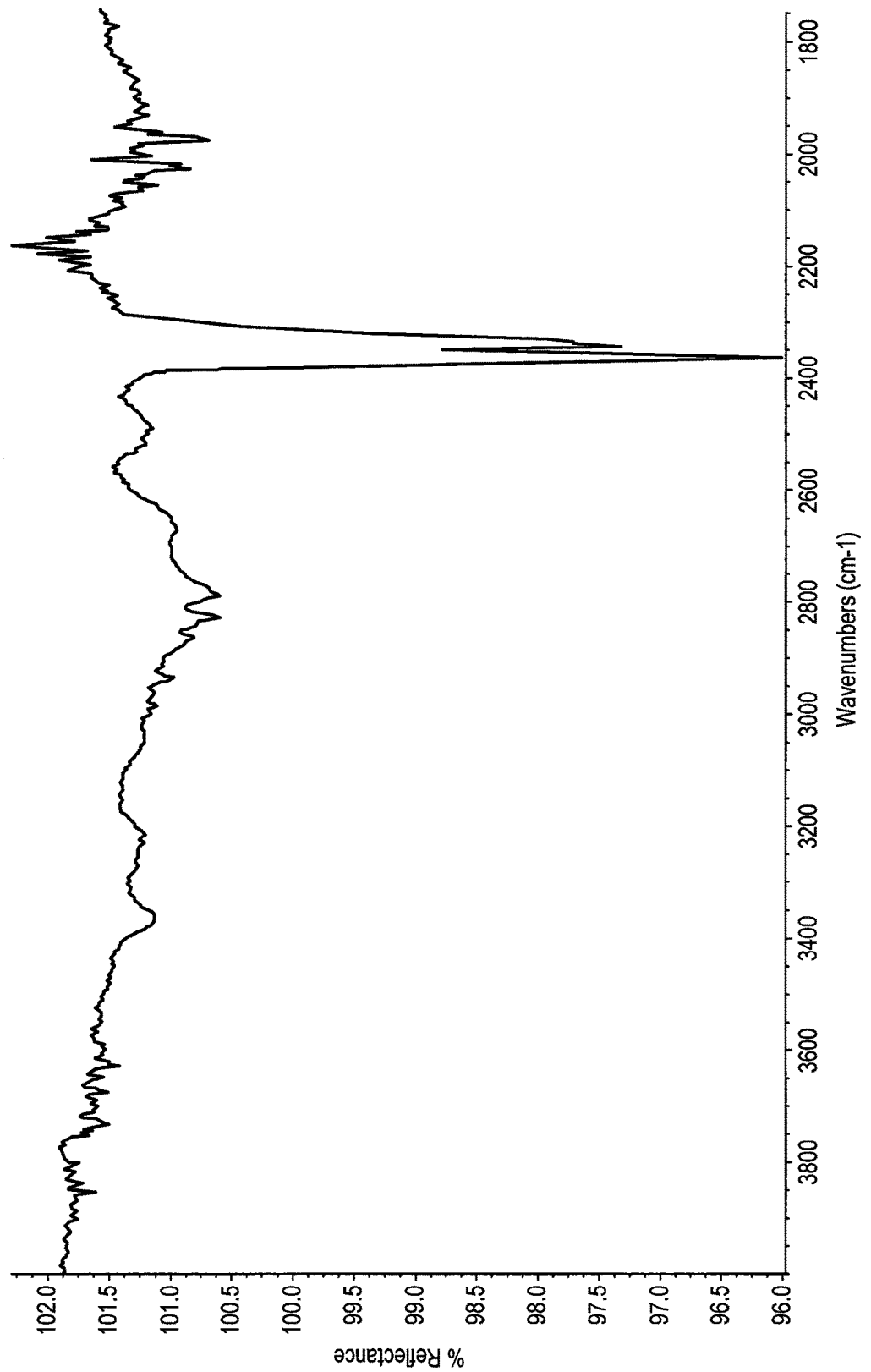
FIG. 2: Crystalline Form IV of minocycline base has a characteristic spectra FTIR (as measured by Fourier Transform Infrared spectroscopy).
Figure 7:
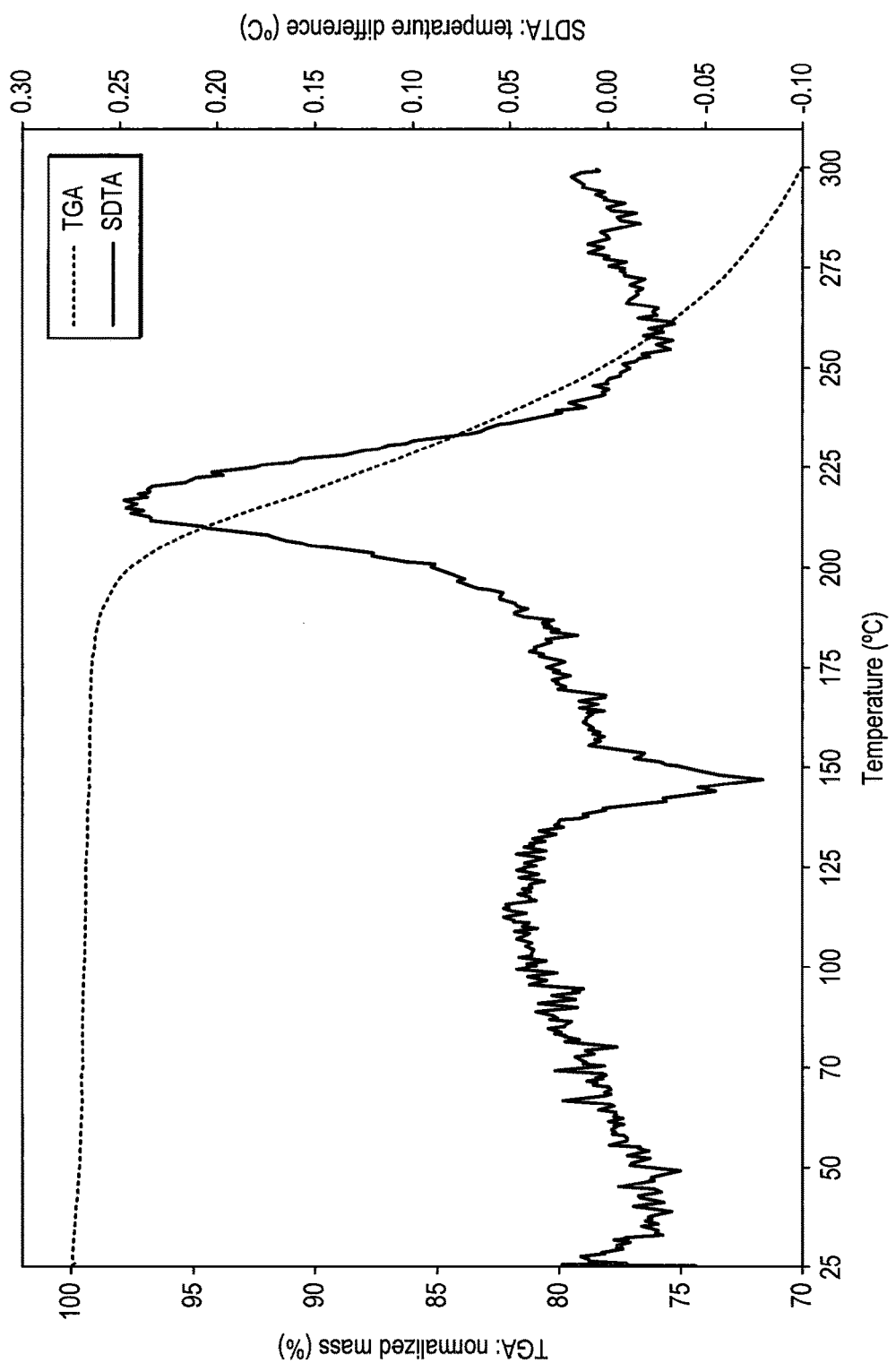
FIG. 7: Crystalline Form IV of minocycline base has a characteristic TGA/SDTA (thermogravimetric analysis).

Crystalline Form IV of minocycline base has a characteristic X-ray diffraction pattern shown in FIG. 1, a FTIR (as measured by Fourier Transform Infrared spectroscopy) spectra of FIG. 2 and TGA/SDTA (Thermogravimetric analysis) as shown in FIG. 7. The SDTA signal is the temperature difference between the temperature measured directly at the sample and the model reference temperature.

For the present invention, the high resolution X-ray powder diffraction patterns were collected on the D8 Advance system equipped with LynxEye solid-state detector. The radiation used for collecting the data was $CuK\alpha 1$ ($\lambda$=1.54056 Å) monochromatized by germanium crystal. The patterns were collected in the range 4 to 50° 2θ, with a step in the range of 0.016° 2θ without further processing. All patterns were taken at approximately 295K.

Data collection was carried out at room temperature using monochromatic $CuK_\alpha$ radiation in the 2θ region between 1.5° and 41.5°, which is the most distinctive part of the XRPD pattern. The diffraction pattern of each well was collected in two 2θ ranges (1.5°≤2θ≤21.5° for the first frame, and 19.5°≤2θ≤41.5° for the second) with an exposure time of 90 s for each frame. No background subtraction or curve smoothing was applied to the XRPD patterns.

The carrier material used during XRPD analysis was transparent to X-rays and contributed only slightly to the background.

For the present invention, mass loss due to solvent or water loss from the crystals was determined by TGA/SDTA. Monitoring the sample weight, during heating in a TGA/SDTA851e instrument (Mettler-Toledo GmbH, Switzerland), resulted in a weight vs. temperature curve. The TGA/SDTA851e was calibrated for temperature with indium and aluminium. Samples were weighed into 100 μl aluminium crucibles and sealed. The seals were pin-holed and the crucibles heated in the TGA from 25 to 300° C. at a heating rate of 10° C. $min^{-1}$. Dry $N_2$ gas was used for purging.

For FTIR in the present invention, FTIR spectra: 4000 a 18000 cm-1

Crystalline Form IV is further characterized by an X-ray diffraction pattern having peaks at 7.06, 8.3, 10.3, 11.18, 13.46, 14.1, 14.94, 16.62, 20.62, 21.3, ±0.2 2θ as depicted in FIG. 1. It is also characterized by an FTIR spectra as shown in FIG. 2 and the SDTA signal of the TGA analysis shows an endotherm at 146° C.

The XRPD results are given below.

| XRPD peak table Form IV | | |
| --- | --- | --- |
| ANGLE (2θ) | D-SPACING | INTENSITY |
| 7.06 | 12.51 | 18.99 |
| 8.3 | 10.64 | 85.38 |
| 10.3 | 8.58 | 21.8 |
| 11.18 | 7.9 | 19.28 |
| 13.46 | 6.57 | 46.64 |
| 14.1 | 6.27 | 27.28 |
| 14.94 | 5.92 | 15.2 |
| 16.62 | 5.33 | 21.33 |
| 20.62 | 4.3 | 9.24 |
| 21.3 | 4.17 | 28.75 |

In another aspect, the invention provides a process for the preparation of polymorphic Form IV of crystalline minocycline base, which process comprises dissolving minocycline base in methyl ethyl ketone (MEK), followed by crystallization as Form IV. Preferably, the process comprises dissolving minocycline base in methyl ethyl ketone cooling the solution to a temperature of from 30° C. to 35° C., the preferred temperature being from 20 to 25° C., and isolating Form IV by crystallization.

Form IV can, for example, also be obtained by dissolving minocycline base in acetonitrile/isopropyl alcohol (50:50 mixture) and evaporating.

Figure 3:
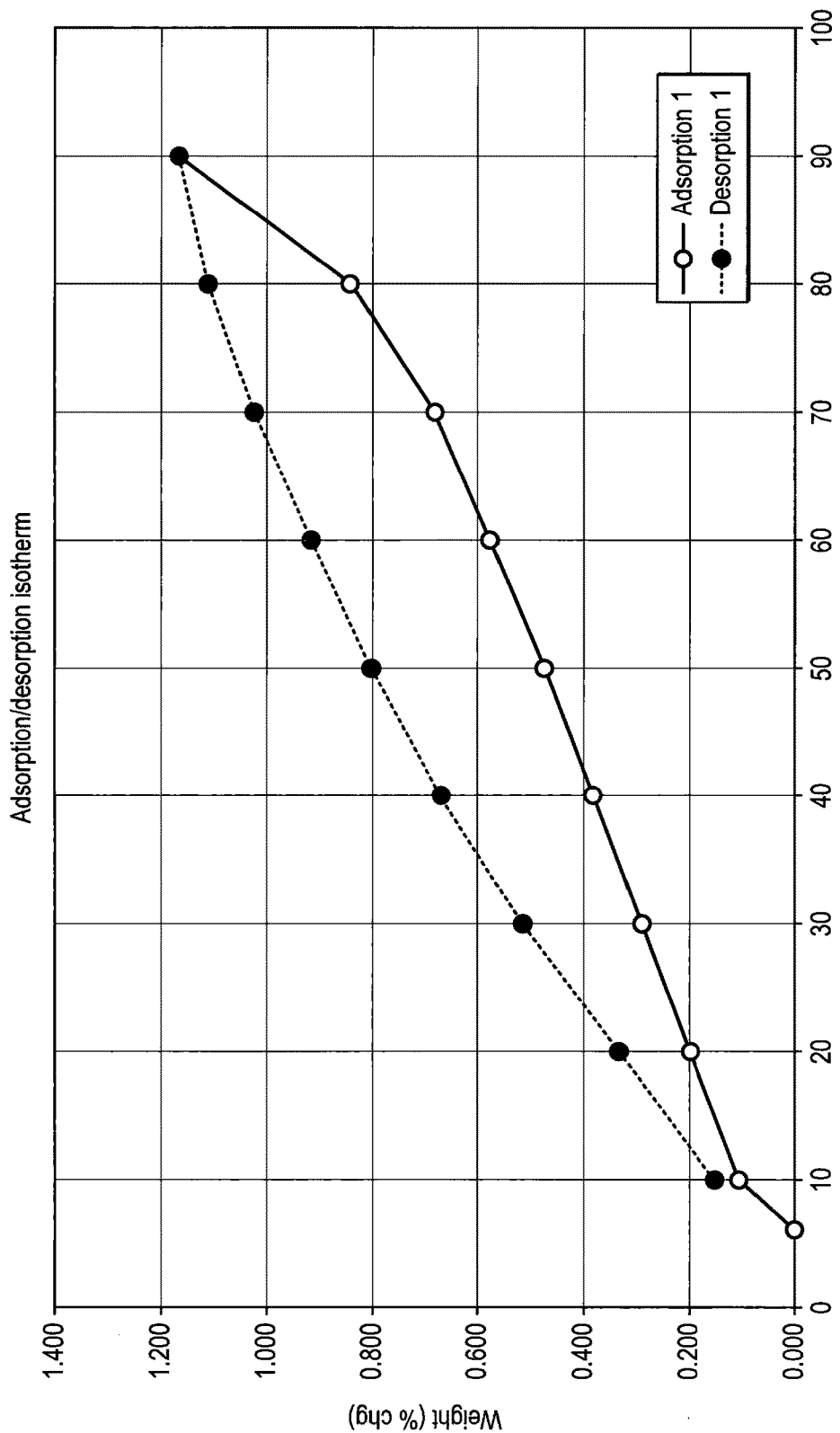
FIG. 3: Crystalline Form IV characterized by an Adsorption/Desorption Isotherm.

Crystalline Form IV is further characterized by an Adsorption/Desorption Isotherm as shown in FIG. 3. This shows the weight change against change in relative humidity.

Figure 4:
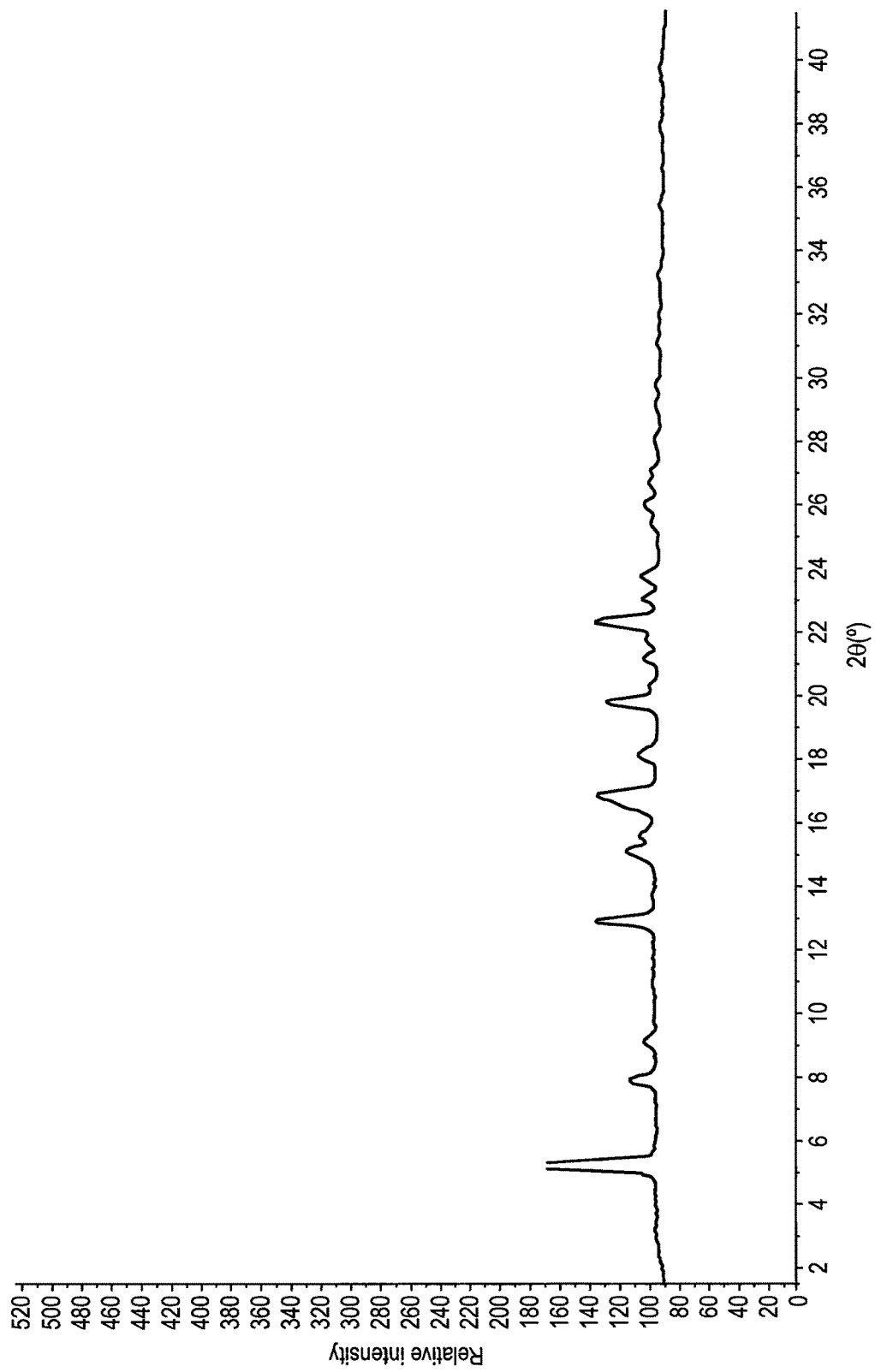
FIG. 4: Crystalline minocycline base form V according to the invention is suitably characterized by an X-ray powder diffraction pattern having peaks.
Figure 5:
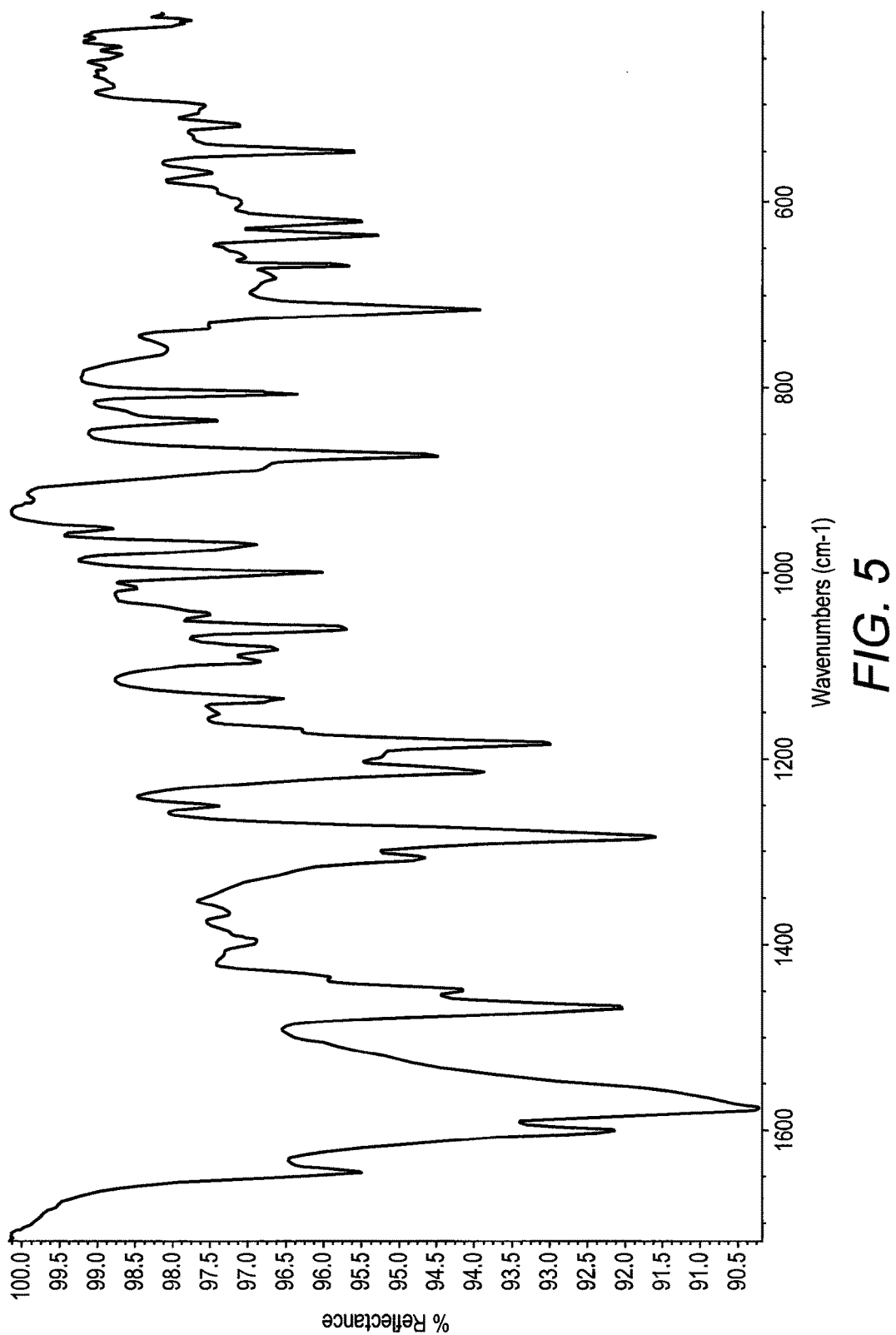
FIG. 5: Crystalline Form V of minocycline base has a characteristic FTIR spectra
Figure 9:
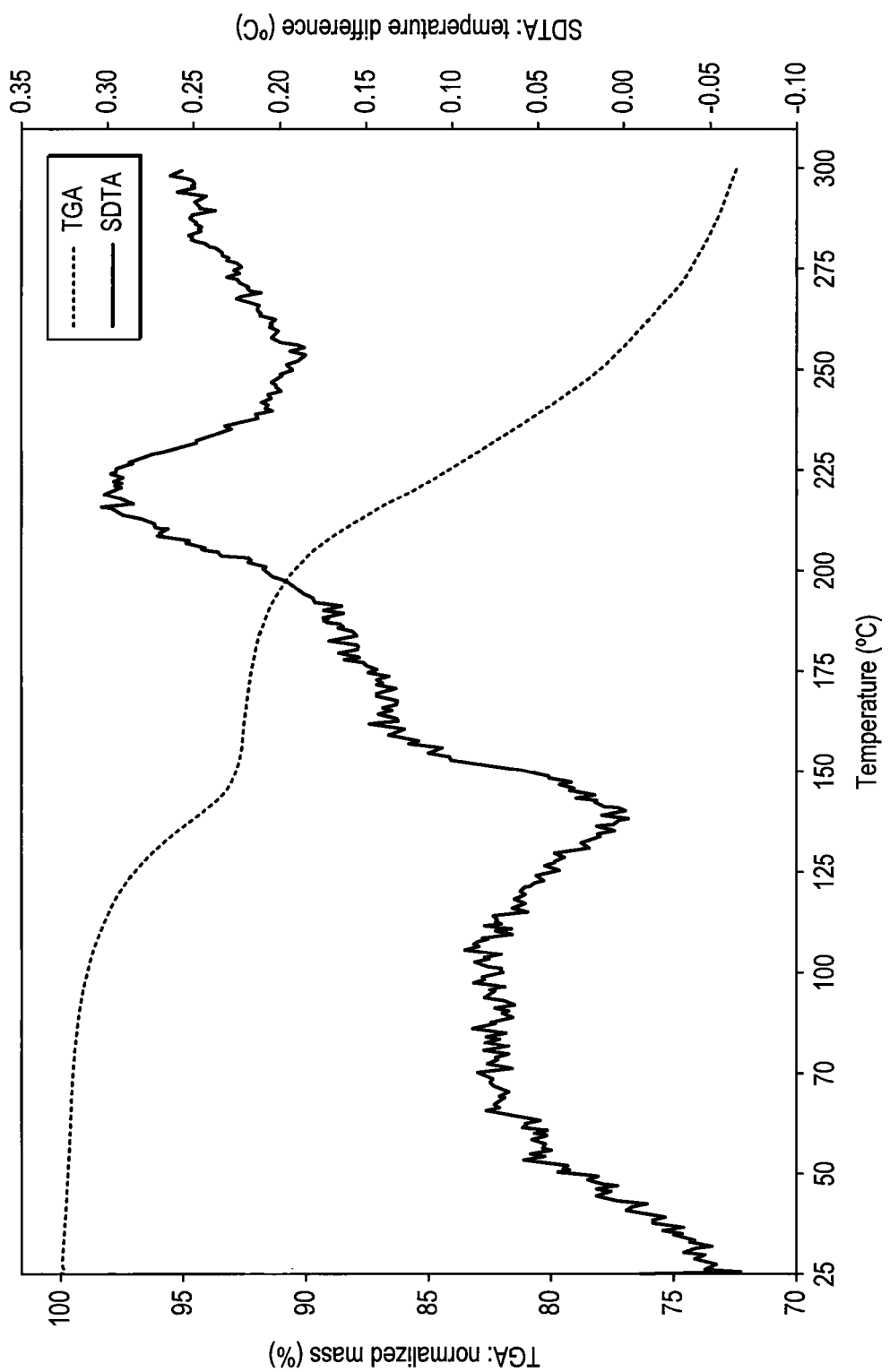
FIG. 9: Crystalline Form V of minocycline base has a characteristic TGA/SDTA.

Crystalline Form V of minocycline base has a characteristic X-ray diffraction pattern shown in FIG. 4 and an FTIR spectra of FIG. 5 and TGA/SDTA as shown in FIG. 9.

Crystalline Form V is further characterized by an X-ray diffraction pattern having peaks at 2.9, 5.34, 7.9, 12.94, 15.06, 16.74, 18.22, 19.78, 21.06, 22.26, 23.02, 25.42±0.2 2θ, as depicted in FIG. 4. It is also characterized by a FTIR spectra depicted in FIG. 5. and the STDA signal of the TGA analysis shows an endotherm at 140° C.

The XRPD results are given below.

| XRPD peak table Form V | | |
| --- | --- | --- |
| ANGLE (2θ) | D-SPACING | INTENSITY |
| 2.9 | 30.43 | 15.6 |
| 5.34 | 16.53 | 64.63 |
| 7.9 | 11.18 | 21.42 |
| 12.94 | 6.83 | 60.3 |
| 15.06 | 5.88 | 23.17 |
| 16.74 | 5.29 | 44.26 |
| 18.22 | 4.86 | 12.36 |
| 19.78 | 4.48 | 33.21 |
| 21.06 | 4.21 | 14.73 |
| 22.26 | 3.99 | 53 |
| 23.02 | 3.86 | 15.72 |
| 25.42 | 3.5 | 9.9 |

In another aspect the invention provides, a process for the preparation of polymorphic Form V of crystalline minocycline base comprises suspending minocycline base in 2-methyl THF (2-methyl tetrahydrofuran) followed by crystallization as Form V.

Preferably, the process comprises suspending minocycline base in 2-methyl THF and applying a thermocycling temperature profile for crystallization.

The thermocycling temperature profile preferably comprises heating the solution three times to a temperature of about 40° C. and cooling each time to about 5° C.

The crystalline minocycline base in Forms IV and V, obtained by the processes described above have a better solubility profile and a more favorable log P than the other known crystalline forms.

Figure 6:
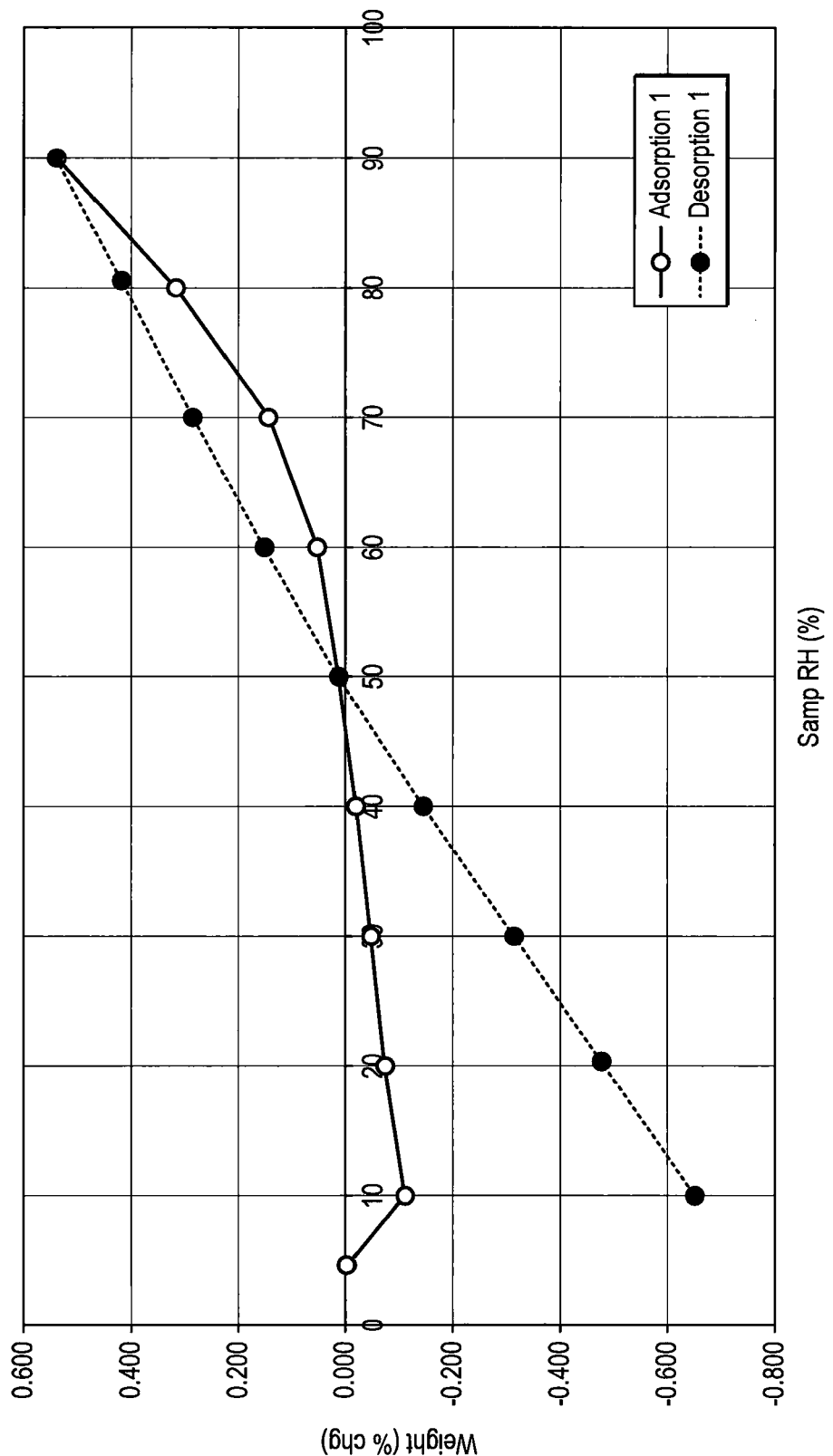
FIG. 6: Crystalline Form V is characterized by an adsorption/Desorption Isotherm.

Crystalline Form V is further characterized by an adsorption/Desorption Isotherm as shown in FIG. 6. This shows the weight change against change in relative humidity.

The solubility of new polymorphic forms IV and V is compared with the solubility known form III (WO2008102161) and the comparison is shown in Table 1. The values show a better solubility of the new polymorphic forms.

Solubility measurements were carried out with buffered solutions prepared at pH=1.2, pH=4.5 and pH=6.8 at a temperature of 37° C.

TABLE 1

Solubilities of crystalline forms of minocycline base

| Crystalline Minocycline base | pH 1.2 TEMP. 37° C. | pH 4.5 TEMP. 37° C. | pH 6.8 TEMP. 37° C. |
|---|---|---|---|
| Form IV | 0.025 g/ml | 0.022 g/ml | 0.0148 g/ml |
| Form V | 0.036 g/ml | 0.023 g/ml | 0.0143 g/ml |
| Form III (WO2008102161) | 0.033 g/ml | 0.018 g/ml | 0.00398 g/ml |

Log P values (i.e. based upon the partition coefficient for minocycline base between the two liquid phases; the Log P value being the logarithm of the ratio of the concentrations of the solute in the liquid phases), showing the distribution of minocycline base between organic and aqueous phase (octanol/water), are depicted in Table 2. The new polymorphic forms IV and V are compared with known form III (WO2008102161) in the table 2. The values show a better solubility in water of the new polymorphic forms. Log P measurements were done in octanol/water at 25° C. and at pH=7.4, with a batch mode. Concentrations were calculated based on UV readings at 246 nm.

TABLE 2

| SAMPLE | Log P |
|---|---|
| Minocycline base crystalline form IV | 0.05 |
| Minocycline base crystalline form V | 0.09 |
| Minocycline base crystalline form III | 0.12 |

In the present invention, minocycline may be used as the base per se or, for example, as an acid addition salt thereof. Preferably, the acid addition salt is non-toxic, and may for example be formed using suitable organic or inorganic acids, for example, sulfonic acid, trichloroacetic acid or hydrochloric acid. Other suitable acids may be used.

The following examples are intended to illustrate the invention, without limiting it in any way.

EXAMPLE 1

Preparation of Crystalline Minocycline Base Form IV

In an inert atmosphere, minocycline base (5 g of Form II as described in WO2008102161) is dissolved in methyl ethyl ketone (50 ml) at a temperature of from 20° C. to 25° C.

The resultant solution was stirred at a temperature of from 20° C. to 25° C.

After about 30 minutes Form IV of crystalline minocycline base precipitates from the solution.

The suspension is stirred for about 10 hours and the product is filtered and dried under vacuum at about 45° C. to yield 3.2 g of crystalline minocycline base—Form IV.

3.2 g of Minocycline base—crystalline Form IV—was obtained.

The new crystalline Form IV shows an endotherm of about 146° C. from the SDTA signal of the TGA analysis depicted in FIG. 7.

EXAMPLE 2

Preparation of Crystalline Minocycline Base Form V

In an inert atmosphere, minocycline base (5 g of Form II as described in WO2008102161) is added slowly to 2 methyl THF (50 ml) at a temperature of from 20° C. to 25° C.

Figure 8:
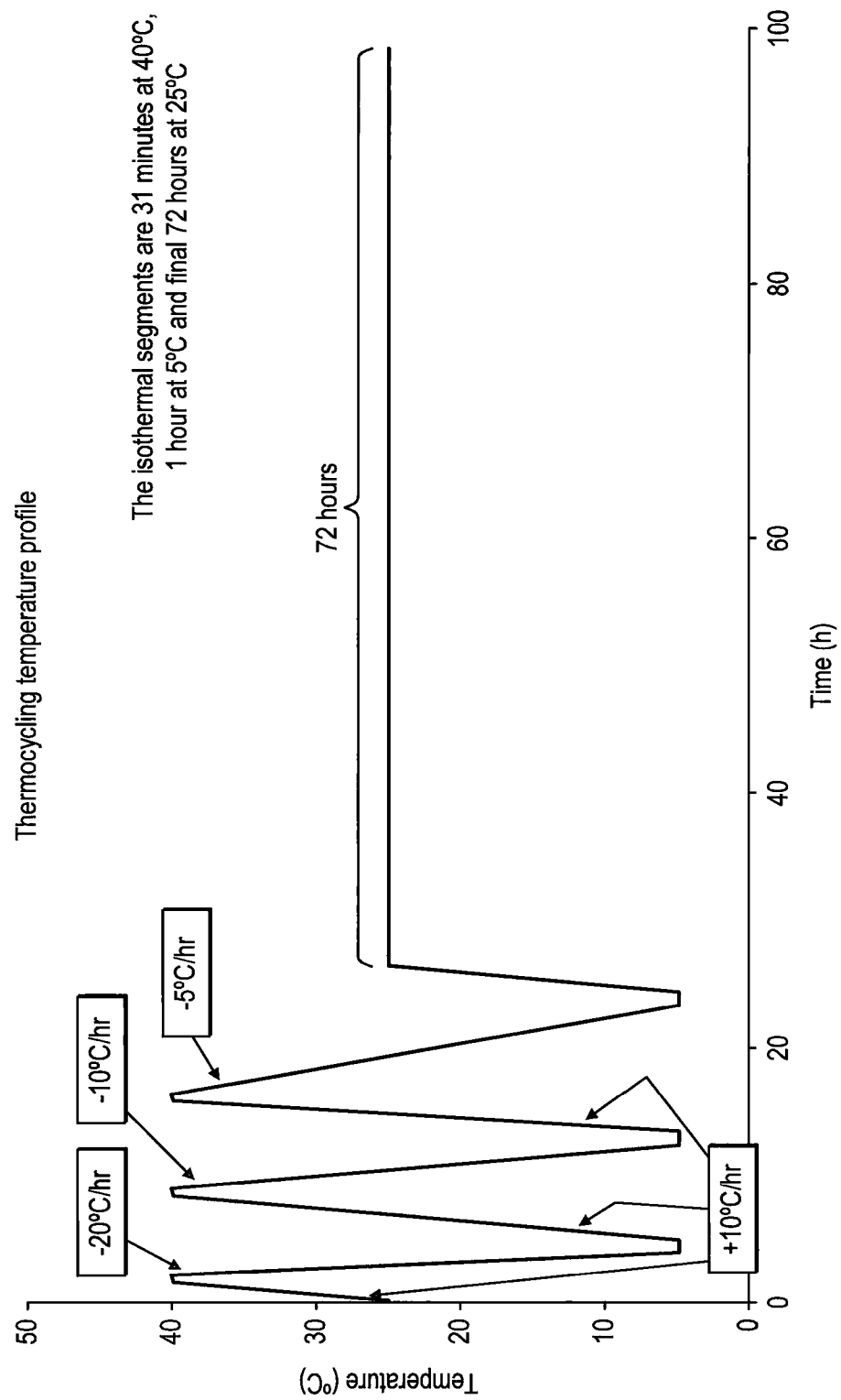
FIG. 8: Crystalline Minocycline Base Form V has a characteristic thermocycling temperature profile.

A suspension is obtained and a thermocycling temperature profile is applied as shown in FIG. 8.

The product is filtered and dried under vacuum at about 45° C. to yield 3.1 g of crystalline minocycline base—Form V.

The new crystalline Form V shows an endotherm at about 140° C. from the SDTA signal of the TGA analysis depicted in FIG. 9.

The invention claimed is:

1. Crystalline minocycline base form IV characterized by an X-ray powder diffraction pattern having peaks at 8.3; 13.46; 14.1, 21.3 and 16.62±0.2° 2θ.

2. Crystalline minocycline base form IV according to claim 1 further characterized by an X-ray powder diffraction pattern having peaks at 7.06, 8.3, 10.3, 11.18, 13.46, 14.1, 14.94, 16.62, 20.62, 21.3 and ±0.2° 2θ.

3. Crystalline minocycline base form IV according to claim 1 characterized by an X-ray powder diffraction pattern having peaks as given in FIG. 1.

4. Crystalline minocycline base form IV according to claim 1, showing an endotherm at 146° C. from the STDA (Signal differential thermal analysis) signal of a TGA (thermogravimetric analysis) analysis.

5. An acid addition salt formed from crystalline minocycline base form IV according to claim 1.

6. A process for preparing minocycline base form IV according to claim 1 characterized by comprising dissolving minocycline base in an aliphatic ketone having 6 carbon atoms or less followed by the precipitation of, and optionally isolation of, form IV.

7. A process according to claim 5 wherein the aliphatic ketone is methyl ethyl ketone (MEK).

8. A process for preparing minocycline base form IV according to claim 6 characterized by a dissolution/precipitation temperature of from 20 to 25° C.

9. A process according to claim 6, characterized in that the solution is stirred for at least 30 mins.

10. A pharmaceutical composition characterized by comprising crystalline minocycline base form IV of claim 1 characterized by an X-ray powder diffraction pattern having peaks at 8.3; 13.46; 14.1, 21.3 and 16.62±0.2° 2θ, or an acid addition salt thereof, and one or more pharmaceutically acceptable excipients.

11. An antibacterial agent comprising a pharmaceutical composition according to claim 10.

12. An anti-inflammatory agent comprising a pharmaceutical composition according to claim 10.

13. A method of treating a bacterial infections, comprising administering to a subject in need thereof, an effective amount of the pharmaceutical composition of claim 10.

14. A method of treating a inflammation, comprising administering to a subject in need thereof, an effective amount of the pharmaceutical composition of claim 10.

\* \* \* \* \*